United States Patent
Liu

(10) Patent No.: US 12,303,381 B2
(45) Date of Patent: May 20, 2025

(54) QUINT-FOCAL DIFFRACTIVE INTRAOCULAR LENS

(71) Applicant: AAREN SCIENTIFIC INC., Ontario (CA)

(72) Inventor: Yueai Liu, Ontario (CA)

(*) Notice: Subject to any disclaimer, the term of this patent is extended or adjusted under 35 U.S.C. 154(b) by 240 days.

(21) Appl. No.: 17/312,792

(22) PCT Filed: Feb. 20, 2020

(86) PCT No.: PCT/US2020/019129
§ 371 (c)(1),
(2) Date: Jun. 10, 2021

(87) PCT Pub. No.: WO2020/132703
PCT Pub. Date: Jun. 25, 2020

(65) Prior Publication Data
US 2022/0133469 A1   May 5, 2022

Related U.S. Application Data

(60) Provisional application No. 62/783,175, filed on Dec. 20, 2018.

(51) Int. Cl.
*A61F 2/16* (2006.01)

(52) U.S. Cl.
CPC .......... *A61F 2/1654* (2013.01); *A61F 2/1618* (2013.01)

(58) Field of Classification Search
CPC ........ A61F 2/1654; A61F 2/1618; A61F 2/16; A61F 2/1637; A61F 2/164; A61F 2/1613; A61F 2/1602; A61F 2/1656; A61F 2/1624; A61F 2250/0053; A61F 2/145; A61F 2/1601; A61F 2/1616; A61F 2/1627; A61F 2/1635; A61F 9/00812; A61F 2/147
See application file for complete search history.

(56) References Cited

U.S. PATENT DOCUMENTS 5,699,142 A   12/1997 Lee et al.
7,156,516 B2   1/2007 Morris et al.
(Continued)

OTHER PUBLICATIONS

International Search Report for PCT/US2020/019129 prepared by the U.S. Patent and Trademark Office, mailing date May 11, 2020.

*Primary Examiner* — Sarah W Aleman
*Assistant Examiner* — Mikail A Mannan
(74) *Attorney, Agent, or Firm* — Kenneth Avila

(57) ABSTRACT

A diffractive quint focal intraocular lens includes a base optic and a diffractive element. The base optic has a base curvature that corresponds to a base power. The diffractive element provides constructive interference in at least five consecutive diffractive orders to create a set of five focal points for vision from near to distance. The constructive interference provides for a near focal point at the highest diffractive order of the five consecutive diffractive orders, a distance focal point at the lowest diffractive order, and three intermediate diffractive orders between the highest and lowest diffractive orders to provide continuity of vision from near to distance with an extended intermediate, an intermediate, and an extended near focal points. The multifocal intraocular lens (i) provides a diffraction efficiency of ~100%, (ii) creates almost no positive optical disturbance, (iii) may also reduce longitudinal chromatic aberration.

5 Claims, 18 Drawing Sheets

(56) References Cited

U.S. PATENT DOCUMENTS

2010/0188636 A1* 7/2010 Pinto .................... G02C 7/044
                                                                 351/159.1
2017/0209259 A1* 7/2017 Choi ..................... G02B 5/1876
2018/0311034 A1 11/2018 Hong et al.

* cited by examiner

| Focal Point (Diffraction Order) | Additional Power (D) | | | |
|---|---|---|---|---|
| Distance (0th) | 0 | 0 | 0 | 0 |
| Extended Intermediate (1st) | 0.5 | 0.75 | 0.8 | 1 |
| Intermediate (2nd) | 1.0 | 1.5 | 1.6 | 2 |
| Extended Near (3rd) | 1.5 | 2.25 | 2.4 | 3 |
| Near (4th) | 2 | 3 | 3.2 | 4 |

| Focal Order | A few Embodiments of Energy Profiles (%) | | | | | | |
|---|---|---|---|---|---|---|---|
| Distance (1st) | 40 | 45 | 50 | 40 | 45 | 40 | 50 |
| Extended Intermediate (2nd) | 10 | 5 | 5 | 12.5 | 10 | 10 | 5 |
| Intermediate (2nd) | 22 | 20 | 10 | 12.5 | 10 | 20 | 20 |
| Extended Near (3rd) | 5 | 10 | 15 | 12.5 | 10 | 10 | 5 |
| Near (4th) | 23 | 20 | 20 | 22.5 | 25 | 20 | 20 |
| Total | 100 | 100 | 100 | 100 | 100 | 100 | 100 |

| Embodiment #1 | Step 1 | Step 2 | Step 3 | Step 4 |
|---|---|---|---|---|
| $\Phi_{i1}$ (wave) | 0 | 0.111 | -0.069 | 0.372 |
| $\Phi_{i2}$ (wave) | 0.523 | 0.534 | 0.426 | 0.502 |

FIG. 8

| Embodiment #1 | $0^{th}$ Order | $1^{st}$ Order | $2^{nd}$ Order | $3^{rd}$ Order | $4^{th}$ Order |
|---|---|---|---|---|---|
| Diffraction Efficiency Estimation (%) | 42 | 8 | 16 | 10 | 22 |

FIG. 9

| Embodiment #2 | Step 1 | Step 2 | Step 3 | Step 4 |
|---|---|---|---|---|
| $\Phi_{i1}$ (wave) | 0.000 | -0.138 | 0.138 | -0.095 |
| $\Phi_{i2}$ (wave) | 0.439 | 0.281 | 0.461 | 0.384 |

FIG. 12

| Embodiment #2 | $0^{th}$ Order | $1^{st}$ Order | $2^{nd}$ Order | $3^{rd}$ Order | $4^{th}$ Order |
|---|---|---|---|---|---|
| Diffraction Efficiency Estimation (%) | 39 | 5 | 21 | 13 | 22 |

FIG. 13

| Embodiment #3 | Step 1 | Step 2 | Step 3 | Step 4 |
|---|---|---|---|---|
| $\Phi_{i1}$ (wave) | 0.000 | -0.031 | 0.145 | -0.145 |
| $\Phi_{i2}$ (wave) | 0.432 | 0.334 | 0.565 | 0.343 |

FIG. 16

| Embodiment #3 | $0^{th}$ Order | $1^{st}$ Order | $2^{nd}$ Order | $3^{rd}$ Order | $4^{th}$ Order |
|---|---|---|---|---|---|
| Diffraction Efficiency Estimation (%) | 41 | 13 | 16 | 8 | 22 |

FIG. 17

| Embodiment #4 | Step 1 | Step 2 | Step 3 | Step 4 |
|---|---|---|---|---|
| $\Phi_{i1}$ (wave) | 0 | 0.111 | -0.069 | 0.372 |
| $\Phi_{i2}$ (wave) | 1.523 | 1.534 | 1.426 | 1.502 |

| Embodiment #5 | Step 1 | Step 2 | Step 3 | Step 4 |
|---|---|---|---|---|
| $\Phi_{i1}$ (wave) | 0.000 | -0.138 | 0.138 | -0.095 |
| $\Phi_{i2}$ (wave) | 1.439 | 1.281 | 1.461 | 1.384 |

| Embodiment #6 | Step 1 | Step 2 | Step 3 | Step 4 |
|---|---|---|---|---|
| $\Phi_{i1}$ (wave) | 0.000 | -0.031 | 0.145 | -0.145 |
| $\Phi_{i2}$ (wave) | 1.432 | 1.334 | 1.565 | 1.343 |

| Focus | Distance | Extended Intermediate | Intermediate | Extended Near | Near |
|---|---|---|---|---|---|
| Diffraction Order | $-2^{nd}$ | $-1^{st}$ | $0^{th}$ | $1^{st}$ | $2^{nd}$ |
| Energy Efficiency (%) | 41 | 10 | 19 | 7 | 23 |

FIG. 25

| Harmonic order | Amplitude $A_i$ | Phase $\Psi_i$ |
|---|---|---|
| 1 | 0.057699 | 0.242119 |
| 2 | 0.234267 | -1.6615 |
| 3 | 0.038004 | -1.4508 |
| 4 | -0.02374 | 1.554965 |
| 5 | 0.027345 | -0.57577 |
| 6 | 0.037391 | -1.51367 |
| 7 | -0.01798 | 1.550559 |
| 8 | -0.01337 | 1.608512 |
| 9 | 0.008417 | -1.02275 |
| 10 | -0.01115 | 1.620449 |
| 11 | -0.00712 | 1.047705 |
| 12 | 0.009787 | -1.29735 |

FIG. 26

QUINT-FOCAL DIFFRACTIVE INTRAOCULAR LENS

CROSS-REFERENCE TO RELATED APPLICATION

This application is the U.S. national phase of PCT Application No. PCT/US2020/019129 filed on Feb. 20, 2020, which claims the benefit of U.S. Provisional Patent Application No. 62/783,175 filed on Dec. 20, 2018, the disclosures of which are incorporated in their entirety by reference herein.

BACKGROUND OF THE INVENTION

1. Field of the Invention

The present invention relates generally to multifocal diffractive lenses, and more particularly to quint-focal diffractive Intraocular Lenses (IOLs). Quint-focal diffractive IOLs have five distinct focal points that provide a patient, who has been implanted with a quint-focal Intraocular Lens (IOL), with distance, extended intermediate, intermediate, extended near, and near vision. Thus, providing patients with a full depth of vision from distance to near.

2. Description of the Related Art

The human crystalline lens is a transparent, biconvex structure in the eye that, along with the cornea, helps to refract light to be focused on the retina. The crystalline lens is flexible, and its curvature is controlled by ciliary muscles that change the curvature of the lens. This process is called accommodation. At shorter focal distance the muscles operate to thicken the crystalline lens, resulting in a rounder shape and thus higher refractive power. At longer focal distances the muscles operate to allow the crystalline lens to relax to reduce the refractive power. An IOL is an artificial lens which is implanted into the human eye following a surgery to remove the natural crystalline lens that has been rendered ineffective by a disease such as cataracts. Usually an IOL does not have the ability to change its shape once it has been implanted and the patient must settle for the focusing abilities of the IOL itself or augment the IOL with another lens such as spectacles or contact lenses.

Early IOLs were monofocal by design and were only able to provide visual focus at a single distance, usually at far distance. As a result, the patient would need to augment the IOL with spectacles or contact lenses to see at intermediate or near distances. As IOL technology advanced, bifocal IOLs became available which provided the patient with two focal points so as to improve a patient's near and distance vision. Further improvements in materials, manufacturing, and computer design software allowed for the construction of diffractive IOLs. These IOLs, using the principle of diffractive constructive interference, allowed for additional focal points to be created. A diffractive bifocal usually creates two focal points with about 82% energy efficiency. A diffractive trifocal IOL would have three focal points, distance and near as a bifocal lens as well as a third focal point for intermediate vision. The intermediate focal point would increase the range of vision for the patient. A diffractive trifocal creates three focal points with about 89% energy efficiency. However, trifocal diffractive IOLs have certain disadvantages. First, they may not be able to provide an intermediate focal point at a comfortable distance for the patient. Second, "holes" or "gaps" in the full range of vision from distance to near would still exist.

Additionally, both the phakic eye and the pseudo-phakic eye suffer from chromatic aberration (CA). CA is a failure of a lens to focus all colors to a particular focal point. The reason for this is that the refractive index of the cornea and the lens, both the natural crystalline lens and the IOL, varies with the wavelength of a color and since the location of a focal point depends on the refractive index, different colors will have different focal points. As a result, the white light image formed at the retina either for the natural phakic eye or pseudophakic eye implanted with an IOL will be blurry.

U.S. Pat. No. 9,320,594, granted to James Schwiegerling, titled "Diffractive Trifocal Lens" discloses a diffractive trifocal IOL comprising an optical element having at least one diffractive surface with a profile comprised of a plurality of annular concentric zones where a distinct step in optical thickness at the junction of adjacent zones defines a step height. The step heights are optimized to produce a phase relationship for constructive interference at three different focal points; distance, intermediate, and near. However, the Schwiegerling lens renders the intermediate vision at ~80 cm for a near distance at ~40 cm which is longer than the OSHA recemented comfortable intermediate range of ~60 cm for computer use. Furthermore, only a portion of the entire range of intermediate vision, from about 50 cm to 180 cm, is covered by the Schwiegerling lens leaving gaps in the intermediate vision where objects are not in focus.

U.S. Pat. No. 10,426,599 granted to Myoung-Taek Choi and others titled "Multifocal lens having reduced chromatic aberrations" discloses an IOL that has an anterior surface, a posterior surface and a diffractive structure providing for four focal points: distance, near, and two intermediates. The lens increases the field of vision in the intermediate range while reducing CA, the entire intermediate range between distance and near is not covered with only two focal points.

US patent publication 2019/0224001, also to Myoung-Taek Choi and others, titled "Multifocal diffractive ophthalmic lens" discloses an IOL with four diffractive orders providing distance, near, and two intermediate focal points. However, one of the intermediate focal points, the 1st order diffraction, is suppressed in order to distribute more energy to the other focal points and thus provide more useful vision. However, the suppression of an intermediate focal point results in the loss of vision detail at that focal point and degrading the patient's range of vision from distance to near intermediate.

Thus, there exists a need for a diffractive IOL that (i) provides diffraction efficiency of ~100% so that the suppression of one or more focal points are not required, (ii) recovers wasted diffraction efficiencies found in existing diffractive IOL designs that are allocated towards useful focal points, (iii) has at least five diffractive orders so that the patient may have a continuity of vision from distance to near, and (iv) reduces CA.

BRIEF SUMMARY OF THE INVENTION

Disclosed is a multifocal IOL having an anterior surface, posterior surface, and at least one diffractive structure including a plurality of either echelettes or Fourier harmonics. The diffractive structure produces constructive interference in at least five consecutive diffraction orders with high energy usage efficiency, to support distance to near vision along with three additional intermediate focal points for a full range of vision between distance and near vision. The design of the diffractive structure may also produce five consecutive diffraction orders, commencing at the 4$^{th}$ order, to support distance to near vision with reduced CA, thus providing patients with high quality white light and color vision.

Other features and advantages of various embodiments of the present invention will be apparent to one skilled in the art from the following description.

BRIEF DESCRIPTION OF DRAWINGS

The present invention will become more fully understood from the detailed description and accompanying drawings, wherein:

FIG. 8 gives a table containing the OPD phase values at the eight ends of the four segments of the diffraction structure for the first embodiment.

FIG. 9 gives a table showing the diffraction efficiency at the 5 consecutive diffraction orders achieved with the diffraction structure of the first embodiment.

FIG. 12 gives a table containing the OPD phase values at the eight ends of the four segments of the diffraction structure for the second embodiment.

FIG. 13 shows diffraction efficiency at the 5 consecutive diffraction orders achieved with the diffraction structure of the second embodiment.

FIG. 16 gives a table containing the OPD phase values at the eight ends of the four segments of the diffraction structure for the third embodiment.

FIG. 17 shows diffraction efficiency at the 5 consecutive diffraction orders achieved with the diffraction structure of the third embodiment.

FIG. 25 gives a table containing the energy distribution amongst the five diffraction orders generated from the diffractive structure of the seventh embodiment. The effective diffraction orders are −2, −1, 0, 1, 2 for distance, extended intermediate, intermediate, extended near, and near vision respectively.

FIG. 26 gives a table containing the amplitudes and phases of the Fourier harmonics.

DETAILED DESCRIPTION OF THE INVENTION

The following description is presented to enable one of ordinary skill in the art to make and use the invention and is provided in the context of a patent application and its requirements. The various embodiments of the present invention provide a multifocal diffractive IOL with improved continuity of vision at intermediate distances. Modifications to the various embodiments described in this specification will be readily apparent and the principles and features disclosed will operate effectively in other configurations such as contact or spectacle lenses without departing from the scope of the invention. Therefore, the present invention is not intended to be limited to the various embodiments shown but is to be accorded the widest scope consistent with the principles and features described herein.

The multifocal diffractive IOL disclosed within this specification has an anterior surface, a posterior surface and at least one diffractive structure including a plurality of echelettes or Fourier harmonics. The various embodiments of the disclosed diffractive structure provide for at least five focal points corresponding to diffractive orders to allow for distance, near, and three stages of intermediate vision. By controlling the energy distribution between the at least five focal points and improving the diffraction efficiency there is no need to suppress any of the diffractive orders and the improved diffraction efficiency decreases the existence of optical dysphotopsia. The said optical dysphotopsia are unwanted optics that may exist in patient's vision after cataract surgery and may be categorized as positive or negative. Positive dysphotopsia is unwanted light, such as a streak, starburst, flicker, fog or haze whereas the less common negative dysphotopsia described as a black line or arc-shaped shadow, in the temporal field of vision. This invention particularly reduces the positive dysphotopsia to its minimum.

Figure 1:
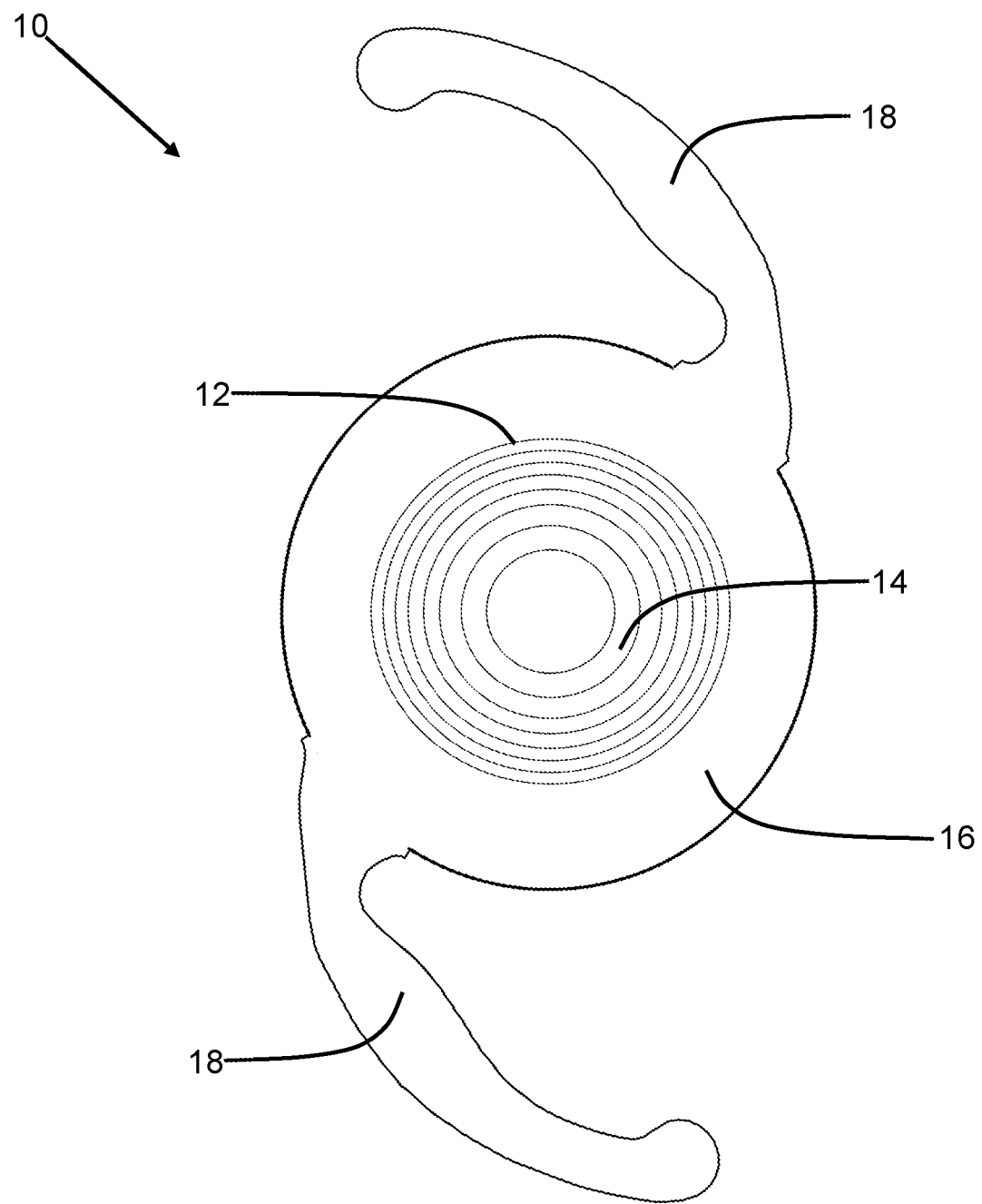
FIG. 1 shows an exemplary schematic plan view of an IOL according to an embodiment of the invention.

FIG. 1 illustrates a particular embodiment of a multifocal diffractive IOL 10 including a diffractive structure 12 on either the anterior or the posterior side of the IOL. Diffractive structure 12 comprises a set of annular diffractive zones 14 wherein each zone comprises a structure suitable for constructive interference of light. The radial width of each diffraction zone 14 controls for additional powers while the step structure within each diffraction zone 14 controls the amount of light diffracted into each of the focal points. Diffractive structure 12 is positioned on base optic 16 which is monofocal and is typically set for distance viewing. IOL 10 includes haptics 18 to hold IOL 10 in place within the capsular bag where previously the crystalline lens would be found. Shown in FIG. 1 are two haptics but IOLs may have more than two haptics or some other sort of structure to hold the IOL in its proper position within the capsular bag. IOL 10, diffractive structure 12, and haptics 18 are typically made from the same flexible materials, such as silicone. Although the disclosed embodiments are described as an IOL, the embodiments may be equally applied to contact lenses and spectacles as well to IOLs that reside in locations of the eye other than the capsular bag.

Figures 2, 3:
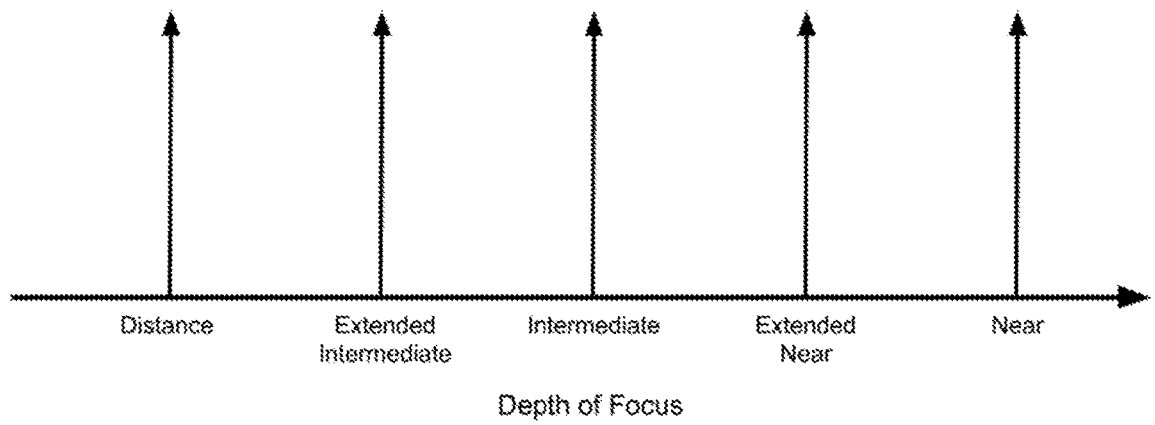
FIG. 2 shows a schematic view of the five consecutive diffraction orders.
FIG. 3 gives a table containing examples of the additional power distribution amongst the five diffraction orders.

It is desirable for an IOL to provide a full depth of vision for the patient so that objects from near, to intermediate, and to distance may be seen in focus. Monofocal IOLs provided patients with a very narrow depth of vision, generally at distance, so that only objects at a far distance are in focus. Bifocal IOLs provided patients with simultaneous vision where objects at near and at distance are in focus. Objects at a near field of vision are those objects that are generally 30 cm to 45 cm in front of the cornea of the eye while objects at a distance field of vision are those objects that are generally at least 400 cm from the eye. The quint focal IOL, represented by IOL 10, seeks to bring into focus those objects that reside between the near and distance fields of vision by use of diffractive structure 12. Diffractive structure 12 introduces a phase perturbation into the optical path to generate five effective diffraction orders to assist patients for vision at distance, extended intermediate, intermediate, extended near, and near distances. FIG. 2 schematically shows, for diffractive structure 12 of IOL 10 disclosed herein, the five focal points that are created: distance, extended intermediate, intermediate, extended near, and near.

FIG. 3 shows a table containing examples of additional power that are useful for presbyopia, that is near vision, correction. The amount of additional power to be crafted onto IOL 10 depends upon the extent of the patient's presbyopia condition, that is the near vision needs of the patient. From the amount of additional power applied to the near vision, the amount of additional power applied to each of the intermediate focal points may be determined where extended intermediate is $\frac{1}{4}$, intermediate is $\frac{1}{2}$, and extended near is $\frac{3}{4}$ of the additional power applied to the near vision. The table in FIG. 3 shows examples where the amount of additional power applied to near vision is 2 D, 3 D, 3.2 D, and 4 D.

Figures 4, 5:
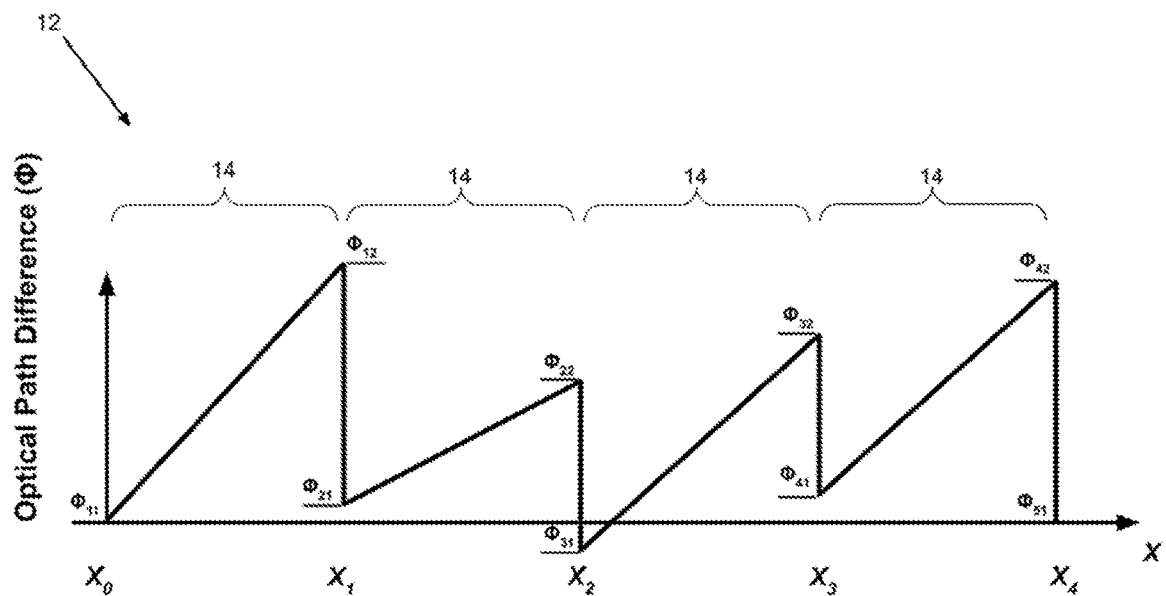
FIG. 4 shows an exemplary diffractive step arrangement of the Optical Path Difference (OPD) of the diffraction structures.
FIG. 5 gives a table containing examples of the energy distribution amongst the five consecutive diffraction orders.

FIG. 4 shows an exemplary micro-structure of diffractive structure 12 of the echelette type where the y-axis, being in the same direction as the optical axis, is shown in terms of optical path difference (OPD) while the x-axis, being the distance from the center of the lens as represented by X, is shown in terms of the radius r squared. The echelette micro-structure of diffractive structure 12 takes the form of a four step repeating diffractive structure that produces a phase relationship for constructive interference at five different focal points; distance, extended intermediate, intermediate, extended near, and near; within the range of vision, with each step being a diffractive zone 14. FIG. 1 shows eight diffraction zones 14 and thus the micro-structure of FIG. 4 has been repeated twice. The radius of each diffraction zone 14 is based on the Fresnel diffractive lens design for the diffraction ring diameter:

$$r_i = \sqrt{\frac{2i\lambda}{ADD}}$$

Where $r_i$ is the radius of the $i^{th}$ zone on the lens; $\lambda$ is the design wavelength; and ADD is the additional power for the near focus. The phase profile of each diffraction zone 14 is a linear line segment in terms of radius $r^2$ with an OPD starting point defined as $\Phi_{i1}$ and an OPD ending point defined as $\Phi_{i2}$. The first diffractive zone 14 from the center of the lens can be chosen as the reference of the OPD, that is $\Phi_{11}$ is defined as zero. As the micro-structure repeats every fourth diffractive zone 14, the value of $\Phi$ at each repeating cycle will be zero. This is shown in FIG. 4 where $\Phi_{11}$ and $\Phi_{51}$ are both zero. The width of each diffractive zone 12 is $X_{i+1} - X_i$ as determined by the Fresnel equation above where X is in terms of radius $r^2$ and i is one of the values 0, 1, 2, or 3. The fraction of incident light energy focused at a particular diffraction order; being 0, +1, +2, +3, and +4; is referred to "diffraction efficiency" for focal points at distance, extended intermediate, intermediate, near intermediate, and near respectively.

This structure is repeated on the lens surface along the direction of radius of the lens aperture. The OPD values at the two ends of each section of the four segments are the design values of the diffraction structure. The OPD distribution of the structure may be expressed with the following equation:

$$OPD(X) = \begin{cases} \Phi_{11} + \frac{(X - X_0)(\Phi_{12} - \Phi_{11})}{\Delta X} & X_0 \le X < X_1 \\ \Phi_{21} + \frac{(X - X_1)(\Phi_{22} - \Phi_{21})}{\Delta X} & X_1 \le X < X_2 \\ \Phi_{31} + \frac{(X - X_2)(\Phi_{32} - \Phi_{31})}{\Delta X} & X_2 \le X < X_3 \\ \Phi_{41} + \frac{(X - X_3)(\Phi_{42} - \Phi_{42})}{\Delta X} & X_3 \le X < X_4 \\ \alpha + \beta X + \gamma X^2 + \delta X^3 & R_D^2 \le X \le R^2 \end{cases}$$

Where $\Delta X = \frac{2\lambda}{ADD}$ $X_0 = 4 \Delta X \, \text{Int}\left(\frac{X}{4 \Delta X}\right)$ $X_1 = X_0 + \Delta X$ $X_2 = X_0 + 2 \Delta X$ $X_3 = X_0 + 3 \Delta X$ $R_D$ is the radius of the diffractive aperture, R is the radius of the lens aperture, n is the initial diffractive order, and the values of $\alpha$, $\beta$, $\gamma$, and $\delta$ are all known in art though $\beta$ is always zero for non-achromatizing first, second, and third embodiments.

The micro-structure of FIG. 4 may be altered to distribute focal energy amongst the five focal points depending upon the needs of the patient. The table in FIG. 5 shows seven different examples of diffraction efficiency at distance or $0^{th}$ diffraction order, extended intermediate or $1^{st}$ diffraction order, intermediate or $2^{nd}$ diffraction order, extended near or $3^{rd}$ diffraction order, and near or $4^{th}$ diffraction order. A particular energy profile can be achieved through optimization to the ten $\Phi_{ij}$ with the help of custom or commercial raytracing software.

Figure 6:
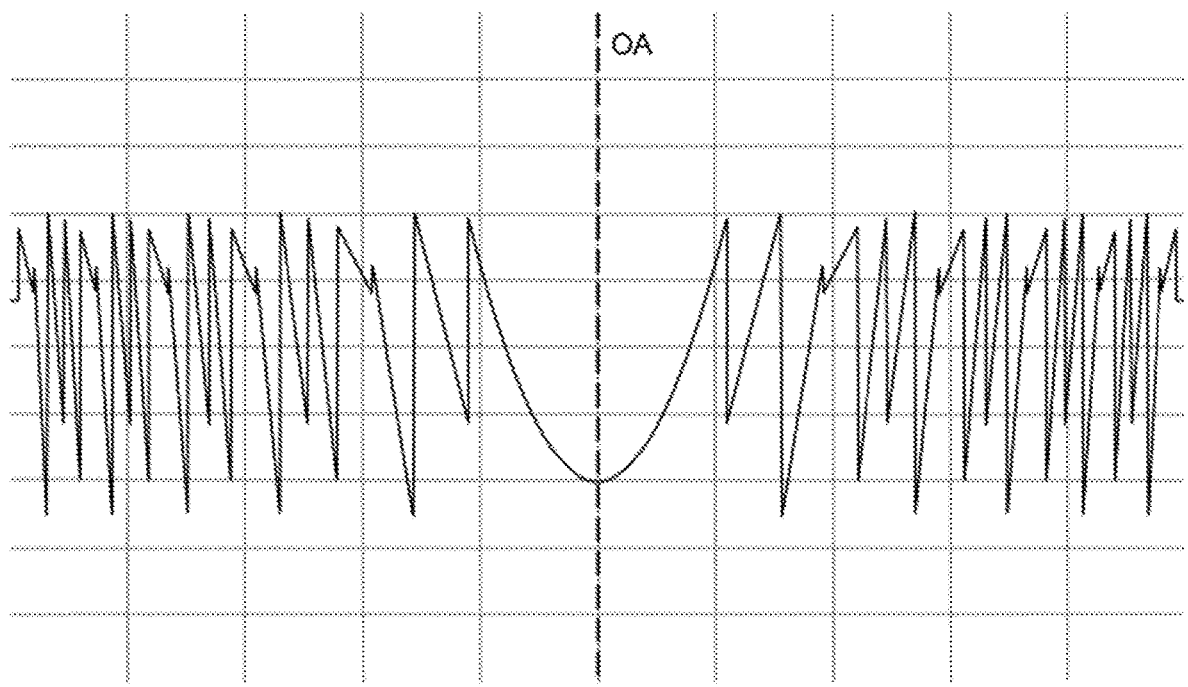
FIG. 6 is a cross-sectional view of the radial OPD phase profile for a diffractive structure according to a first embodiment of the disclosed diffractive lens.
Figure 7:
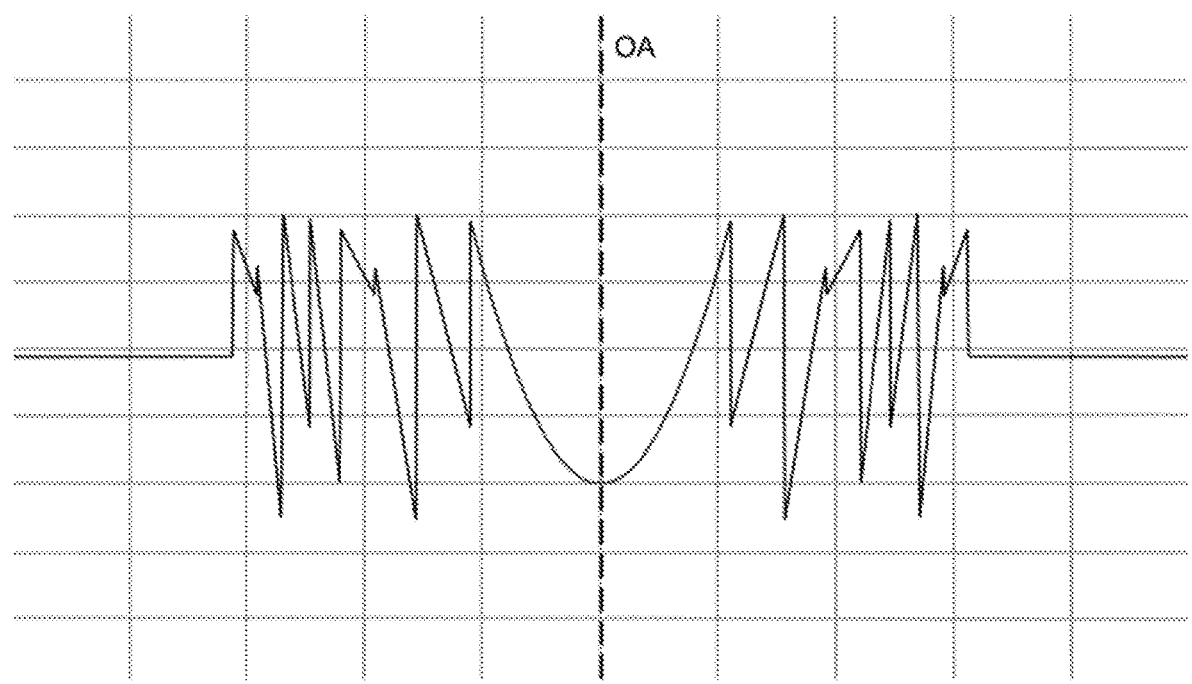
FIG. 7 is a cross-sectional view of the radial OPD phase profile for the diffractive structure of the first embodiment having a partial diffraction aperture. It is effectively the diffraction structure of the first embodiment apodised with a top-hat function.
Figure 10:
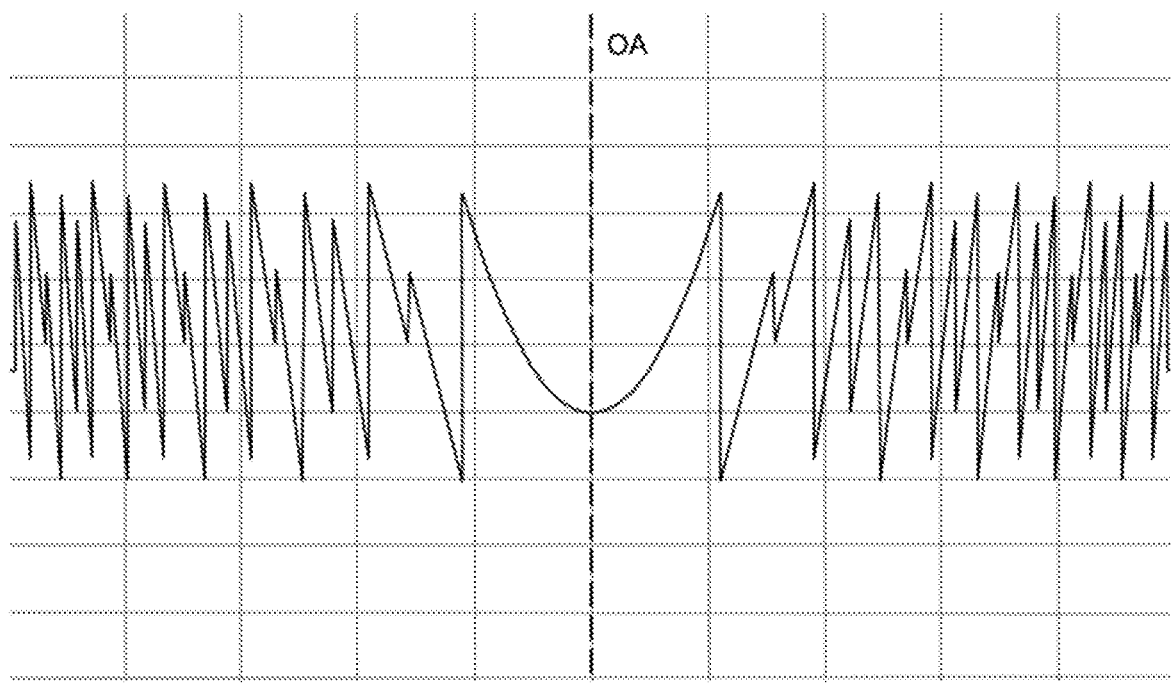
FIG. 10 is a cross-sectional view of the radial OPD phase profile for a diffractive structure according to a second embodiment of the disclosed diffractive lens.
Figure 11:
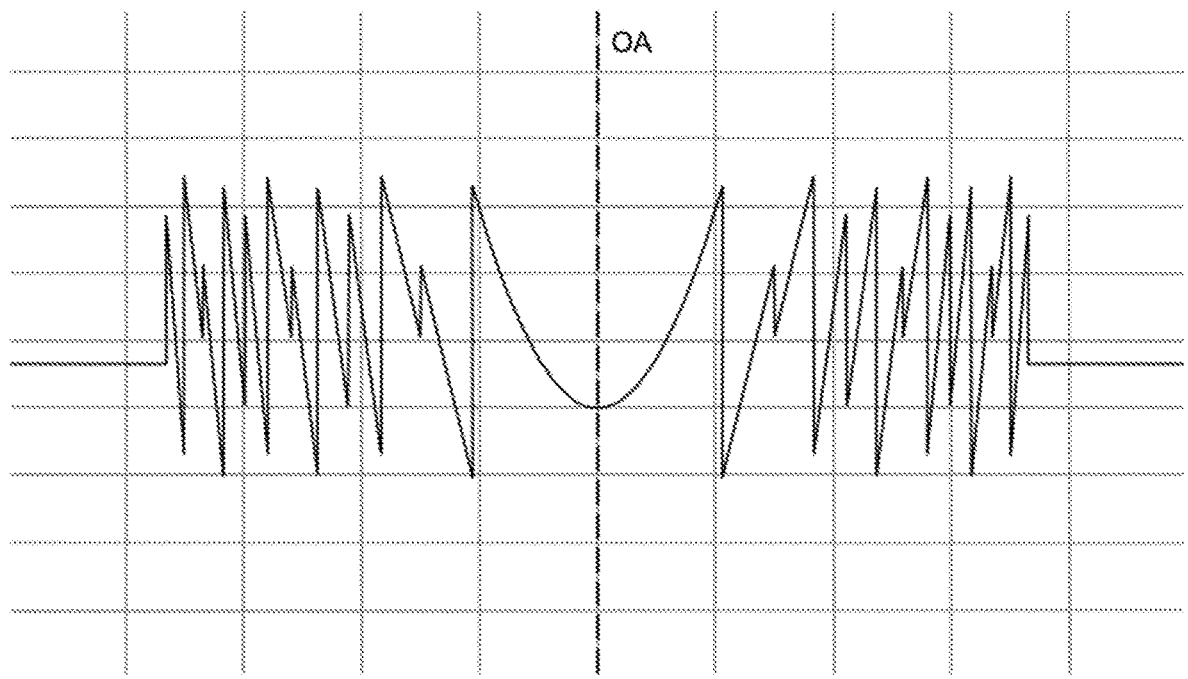
FIG. 11 is a cross-sectional view of the radial OPD phase profile for the diffractive structure of the second embodiment having a partial diffraction aperture. It is effectively the diffraction structure of the second embodiment apodised with a top-hat function.
Figure 14:
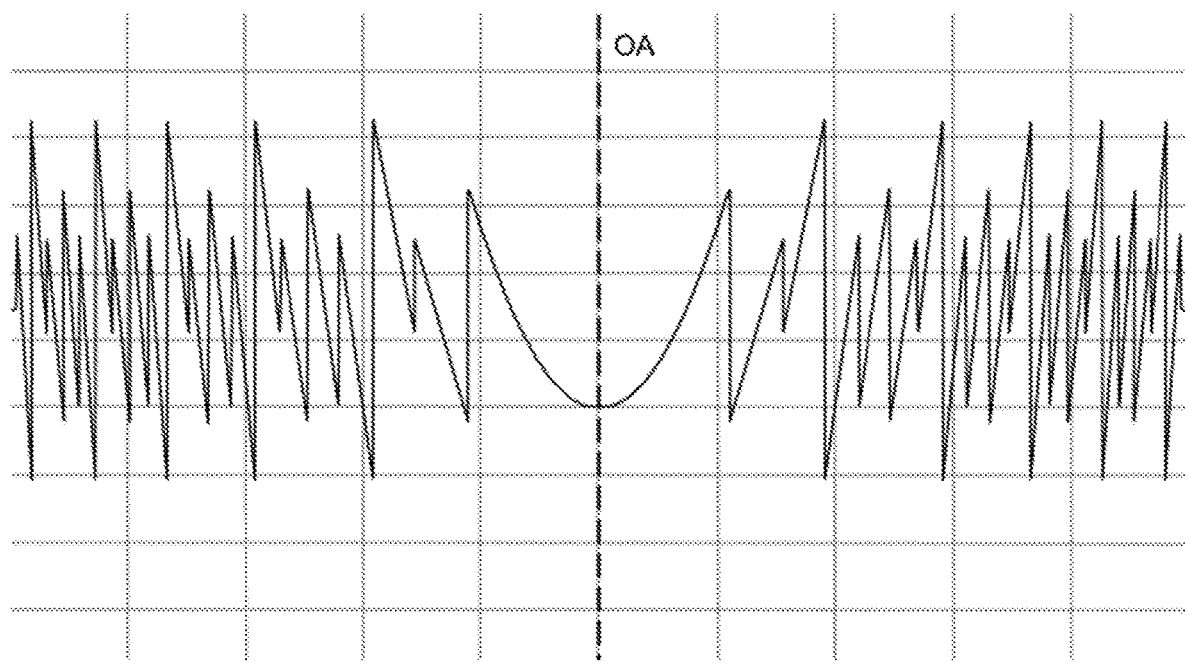
FIG. 14 is a cross-sectional view of the radial OPD phase profile for a diffractive structure according to a third embodiment of the disclosed diffractive lens.
Figure 15:
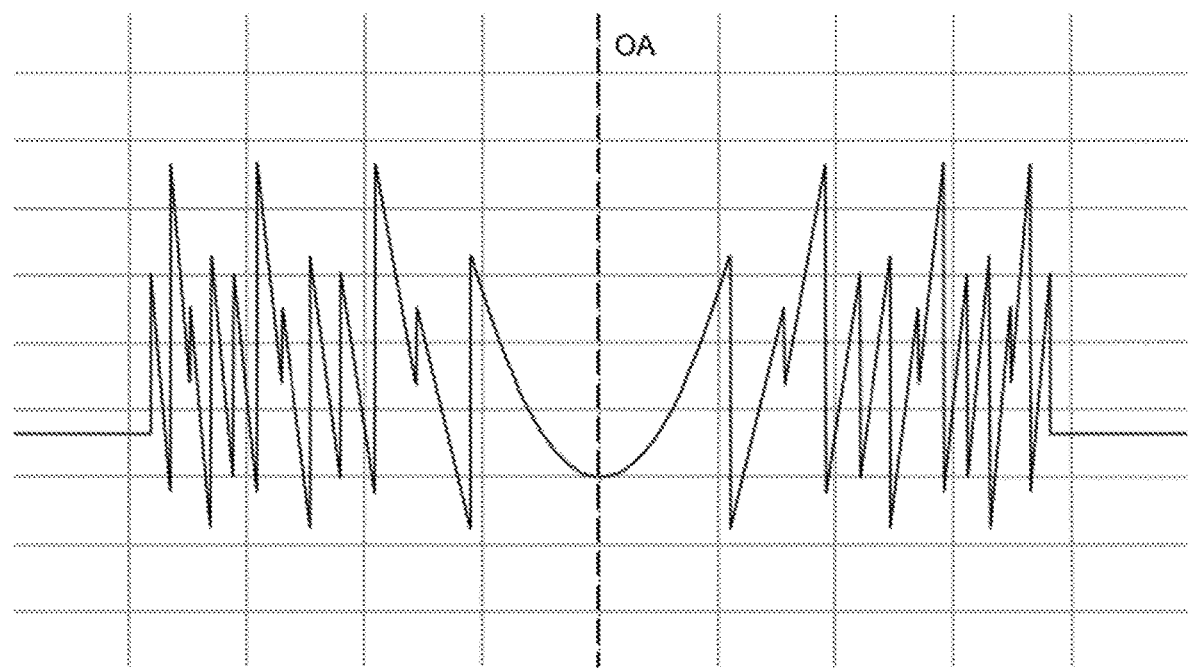
FIG. 15 is a cross-sectional view of the radial OPD phase profile for the diffractive structure of the third embodiment having a partial diffraction aperture. It is effectively the diffraction structure of the third embodiment apodised with a top-hat function.

FIGS. 6, 10, and 14 shows the OPD phase profile of diffractive structure 12 for the first, second, and third embodiments respectively of the quint focal IOL. The phase profile is illustrated as a plurality of diffraction zones 14 about optical axis OA, shown as a dashed line, where the radial location is zero. As diffraction zones 14 are annular rings about the optical axis the OPD phase profile is symmetrical about optical axis OA. Each diffraction zone 14 is bounded on either side by a vertical step and each set of four diffraction zones 14, starting from the first diffraction zone closest to optical axis OA, is represented by the step structure of FIG. 4. The step structure in FIG. 4 shows the diffraction zones along the radius of the lens aperture starting from the optical axis OA. The diffractive phase profile is separated from the refractive portion of base optic 16 (i.e., zero on the vertical axis corresponds to the surface of base optic 16). The OPD phase profile shows five repeating sets of the four diffraction zones represented by FIG. 4. This discussion also applies to FIGS. 7, 11, and 15 where the OPD phase profile of diffractive structure 12 for the first, second, and third embodiments respectively of the quint focal IOL is apodised by a top hat function.

FIGS. 8, 12, and 16 give a table containing the OPD phase values at the eight ends of the four diffraction zones 14 of diffraction structure 12 as shown in FIG. 4 for the first, second, and third embodiments respectively of the quint focal IOL. The column Step 1 shows the OPD phase values for the range $X_0$ to $X_1$ being $\Phi_{11}$ and $\Phi_{12}$ respectively. The column Step 2 shows the OPD phase values for the range $X_1$ to $X_2$ being $\Phi_{21}$ and $\Phi_{22}$ respectively. The column Step 3 shows the OPD phase values for the range $X_2$ to $X_3$ being $\Phi_{31}$ and $\Phi_{32}$ respectively. Finally, the column Step 4 shows the OPD phase values for the range $X_3$ to $X_4$ being $\Phi_{41}$ and $\Phi_{42}$ respectively. The OPD phase values are repeated for each set of the four diffraction zones 14 shown in FIG. 4. FIG. 1 shows IOL 10 with eight diffraction zones 14 thus twice repeating the OPD phase values given in the tables.

FIGS. 9, 13, and 17 give a table containing an estimation of the diffraction efficiency at the 5 consecutive diffraction orders achieved with the diffraction structure of the first, second, and third embodiments respectively of the quint focal IOL at photopic aperture. In the figures the reader may see that the first, second, and third embodiments of IOL 10 provides excellent efficiency at both distance ($0^{th}$ order) and near ($4^{th}$ order) focal points while broadly spreading the efficiency at the three intermediate focal points ($1^{st}$, $2^{nd}$ and $3^{rd}$ orders). One with ordinary skill in the art would appreciate that the diffraction efficiencies may be shifted between the five orders by a change of the OPD values in diffraction structure 12. In this manner vision may be improved at any one of the five diffraction focal point at the expense of vision in the remaining focal points in order to best adapt the IOL to the lifestyle of the patient.

The first, second, and third embodiments of the quint focal IOL may be converted to an achromatizing version to reduce the CA of the pseudophakic eye by a change of the energy producing diffraction orders. The first, second, and third embodiments of the quint focal IOL all use, as the energy producing diffraction orders, the $0^{th}$ diffractive order for distance vision and the $4^{th}$ diffractive order for near vision. The achromatizing version of the first, second, and third embodiment, being the fourth, fifth, and sixth embodiments herein, use as the energy producing diffraction orders, the $4^{th}$ for distance vision, $8^{th}$ for near vision, and $5^{th}$, $6^{th}$, and $7^{th}$ diffraction orders for the intermediate focal points. The diffraction efficiency estimation of the first, second, and third embodiments shown in FIGS. 9, 13, and 17 respectively, remain the same for the achromatizing fourth, fifth, and sixth embodiments.

Figures 18, 19:
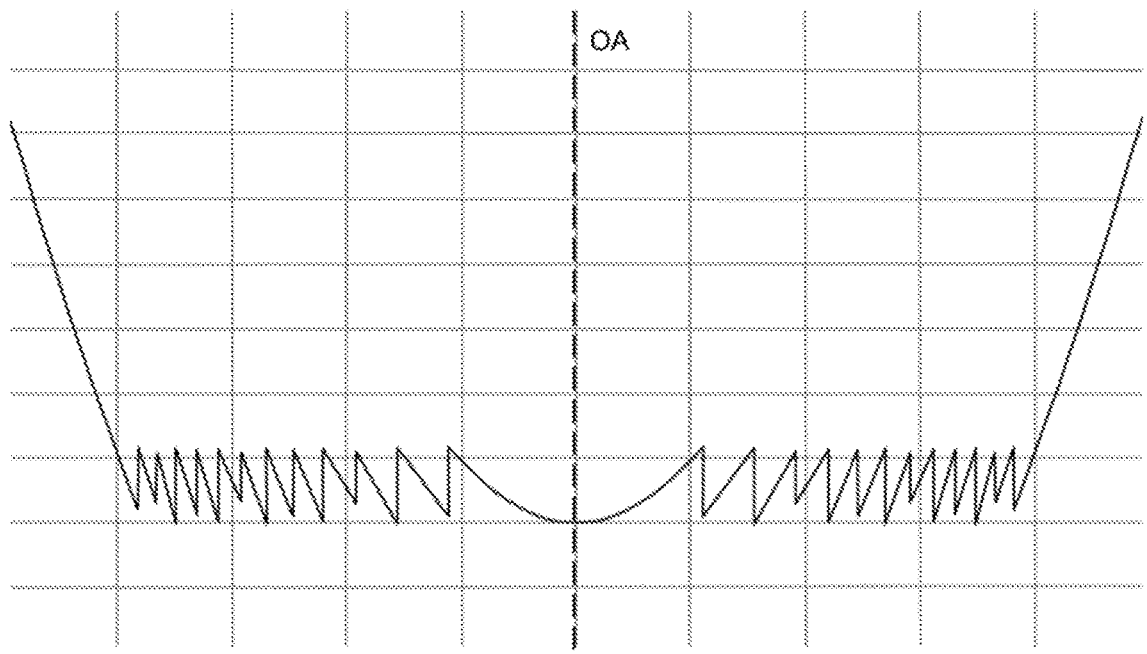
FIG. 18 is a cross-sectional view of the radial OPD phase profile for the diffractive structure of the fourth embodiment having a partial diffraction aperture. It is effectively the achromatizing version of the first embodiment with a partial diffraction aperture.
FIG. 19 gives a table containing the OPD phase values at the eight ends of the four segments of the diffraction structure for the fourth embodiment.
Figures 20, 21:
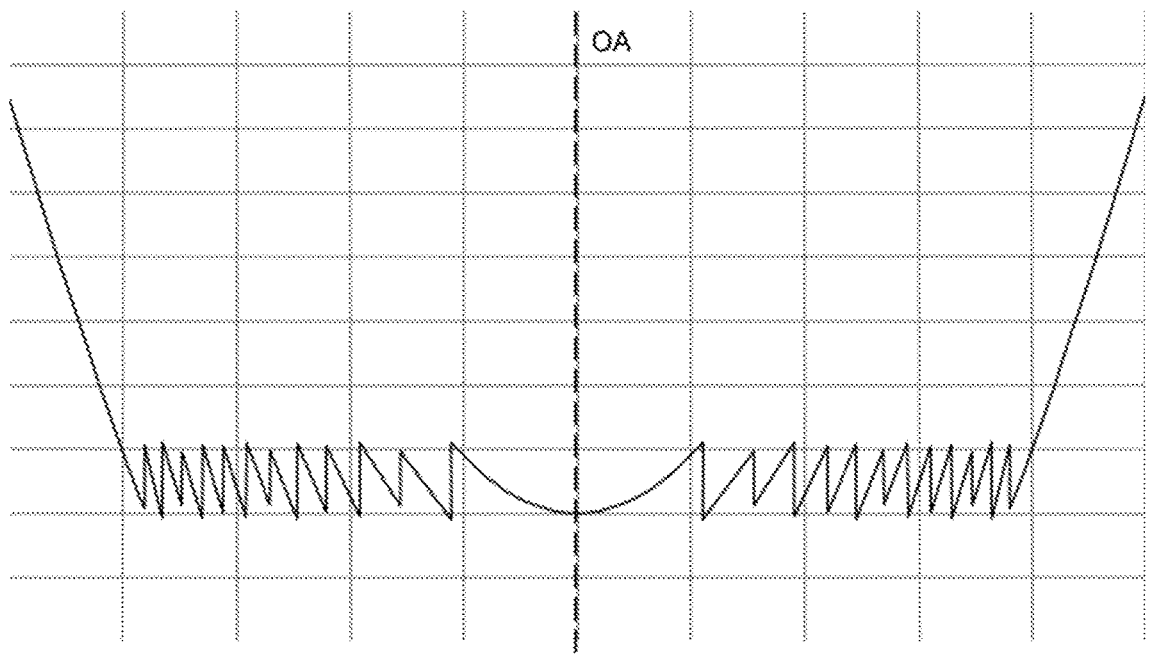
FIG. 20 is a cross-sectional view of the radial OPD phase profile for the diffractive structure of the fifth embodiment having a partial diffraction aperture. It is effectively the achromatizing version of the second embodiment with a partial diffraction aperture.
FIG. 21 gives a table containing the OPD phase values at the eight ends of the four segments of the diffraction structure for the fifth embodiment.
Figures 22, 23:
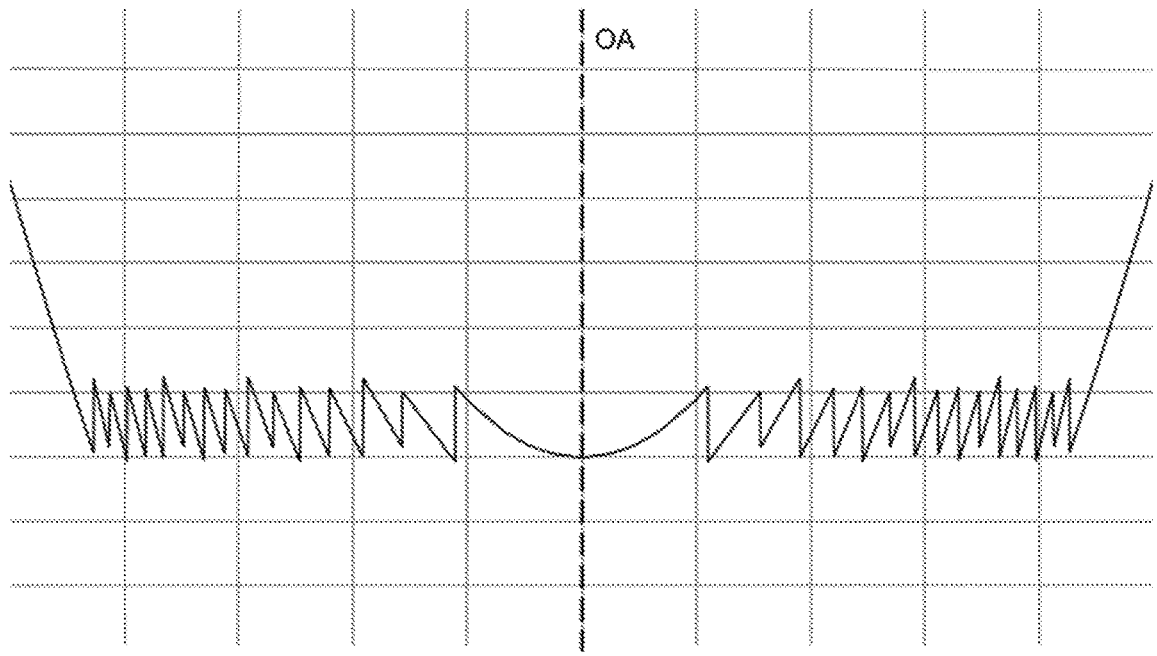
FIG. 22 is a cross-sectional view of the radial OPD phase profile for the diffractive structure of the sixth embodiment having a partial diffraction aperture. It is effectively the achromatizing version of the third embodiment with a partial diffraction aperture.
FIG. 23 gives a table containing the OPD phase values at the eight ends of the four segments of the diffraction structure for the sixth embodiment.

FIGS. 18, 20, and 22 shows the achromatizing phase profile of diffractive structure 12 for the fourth, fifth, and sixth embodiments respectively of the quint focal IOL. The OPD phase profile is illustrated as a plurality of diffraction zones 14 about optical axis OA, shown as a dashed line, where the radial location is zero. As diffraction zones 14 are annular rings about the optical axis the OPD phase profile is symmetrical about optical axis OA. Each diffraction zone 14 is bounded on either side by a vertical step and each set of four diffraction zones 14, starting from the first diffraction zone closest to optical axis OA, is represented by the step structure of FIG. 4. The phase profile is separated from the refractive portion of base optic 16 (i.e., zero on the vertical axis corresponds to the surface of base optic 16). The phase profile shows three repeating sets of the four diffraction zones represented by FIG. 4.

FIGS. 19, 21, and 23 give a table containing the OPD phase values at the eight ends of the four diffraction zones 14 of diffraction structure 12 as shown in FIG. 4 for the fourth, fifth, and sixth embodiments respectively of the quint focal IOL. The column Step 1 shows the OPD phase values for the range $X_0$ to $X_1$ being $\Phi_{11}$ and $\Phi_{12}$ respectively. The column Step 2 shows the OPD phase values for the range $X_1$ to $X_2$ being $\Phi_{21}$ and $\Phi_{22}$ respectively. The column Step 3 shows the OPD phase values for the range $X_2$ to $X_3$ being $\Phi_{31}$ and $\Phi_{32}$ respectively. Finally, the column Step 4 shows the OPD phase values for the range $X_3$ to $X_4$ being $\Phi_{41}$ and $\Phi_{42}$ respectively. The OPD phase values are repeated for each set of the four diffraction zones 14 shown in FIG. 4. FIG. 1 shows IOL 10 with eight diffraction zones 14 thus twice repeating the OPD phase values given in the tables.

The manufacturing of diffractive structure 12 of quint focal IOL 10 may be simplified by the application of sinusoidal Fourier harmonics to diffractive structure 12. The diffraction structures in embodiments discussed thus far, embodiments one through six, consists of a plurality of echelettes. The following embodiments, seven and eight, consists of a plurality of Fourier harmonics. The application of the Fourier harmonics smooths the step structure shown in FIG. 4 to eliminate the sharp contours while retaining the diffraction efficiency of diffractive structure 12 at ~100%. The OPD distribution of the sinusoidal Fourier harmonics exemplary can be exemplified with the following equation:

$$OPD(X) = \begin{cases} \sum_{1}^{N} A_i \cos\left(\frac{i\pi \text{ADD}}{4}X + \Psi_i\right) & X \leq R_D^2 \\ \alpha + \beta X + \gamma X^2 + \delta X^3 & R_D^2 \leq X \leq R^2 \end{cases}$$

Where ADD is the near additional power and the values of N, $A_i$, $\psi_i$, $\alpha$, $\beta$, $\gamma$, and $\delta$ are all parameters to be optimized for the design goals of the quint focal IOL.

Figure 24:
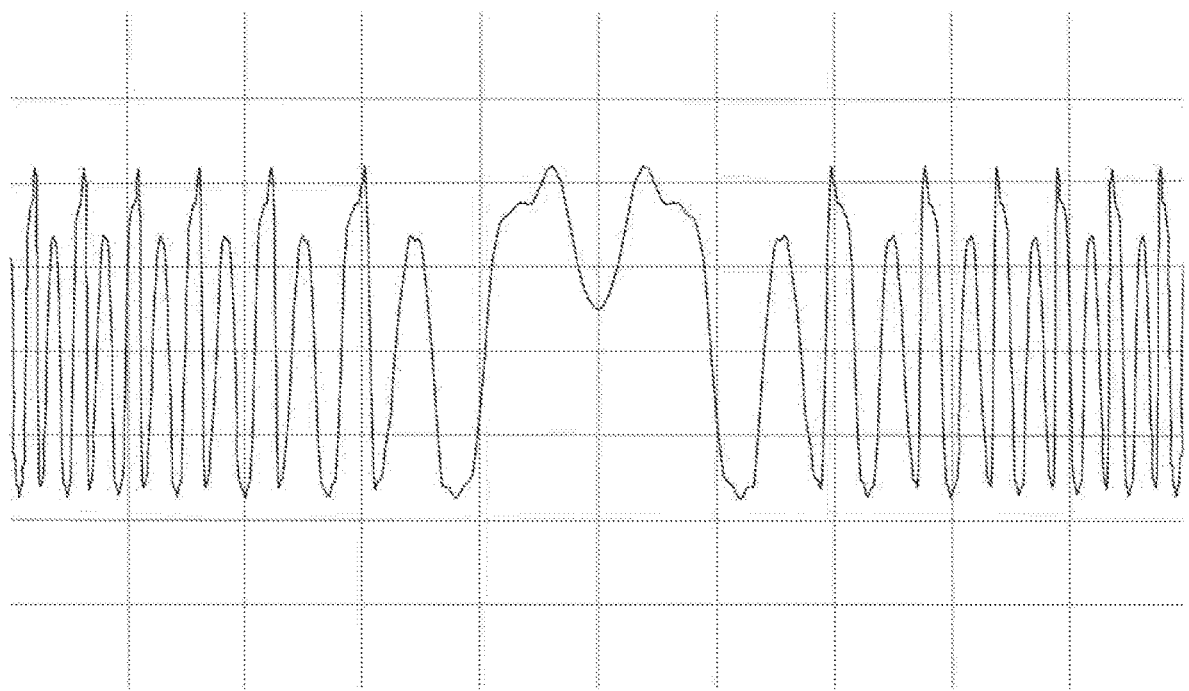
FIG. 24 is a cross-sectional view of the radial OPD phase profile for the diffractive structure of the seventh embodiment having a Fourier Harmonics.
Figure 27:
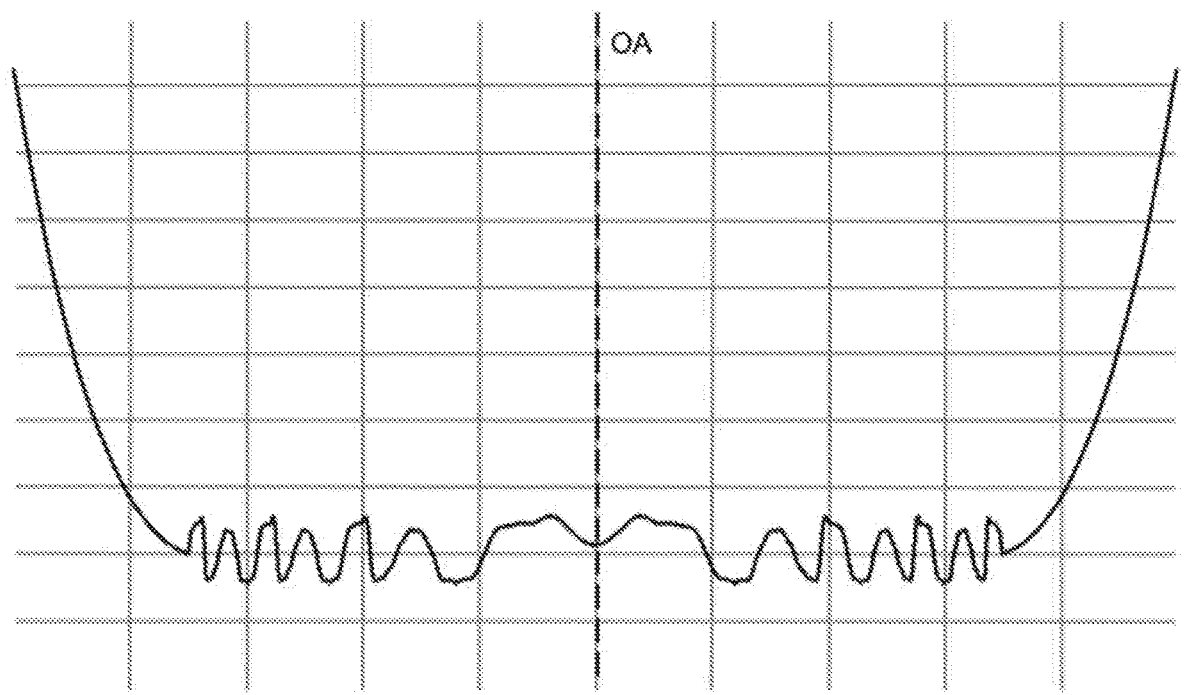
FIG. 27 is a cross-sectional view of the radial OPD phase profile for the diffractive structure of the eighth embodiment having a Fourier Harmonics which is effectively the partial diffractive aperture version of the seventh embodiment.

FIG. 24 shows the OPD phase profile of a diffractive structure 12 modified by the application of twelve sinusoidal Fourier harmonics as embodiment eight of the quint focal IOL. The application of the sinusoidal Fourier harmonics shifts the effective diffraction orders from 0, +1, +2, +3, and +4 to −2, −1, 0, +1, and +2 where −2 diffraction order is for distance, −1 diffraction order is for extended intermediate, 0 diffraction order is for intermediate, +1 is for extended near, and +2 is for near vision respectively. The OPD phase profile is illustrated as a plurality of diffraction zones 14 about optical axis OA, shown as a dashed line, where the radial location is zero. As diffraction zones 14 are annular rings about the optical axis the OPD phase profile is symmetrical about optical axis OA. The OPD phase profile is separated from the refractive portion of base optic 16 (i.e., zero on the vertical axis corresponds to the surface of base optic 16). FIG. 25 gives a table containing the diffraction efficiencies for each of the diffraction orders: −2, −1, 0, +1, and +2, in this embodiment. FIG. 26 gives a table listing the amplitudes and phases of the sinusoidal Fourier harmonics applied to the quint focal IOL. FIG. 27 shows a cross-sectional view of the radial OPD phase profile for the diffractive structure of this embodiment apodised by a top hat function which is effectively the partial diffractive aperture version of the seventh embodiment.

Although a number of embodiments have been illustrated and described herein, it will be appreciated by those of ordinary skill in the art that a wide variety of equivalent embodiments or implementations calculated to achieve the same purposes may be substituted for the embodiments disclosed herein without departing from the scope of the present invention. Those with skill in the art will readily appreciate that embodiments in accordance with the present invention may be implemented in a very wide variety of ways. This application is intended to cover any adaptations or variations of the embodiments discussed herein.

The terms and expressions which have been employed in this specification are used as terms of description and not of limitation, and there is no intention, in the use of such terms and expressions, to exclude equivalents of the features shown and described or portions thereof, it being recognized that the scope of the invention is defined and limited only by the claims that follow.

What is claimed is:

1. An intraocular lens comprising:
a lens having an anterior surface and a posterior surface and
a diffractive profile disposed on at least one of the anterior surface and the posterior surface, the diffractive profile comprising one or more annular zones about the optical axis of the lens, where each annular zone having four annular subzones, where each annular subzone comprises a diffractive step, the annular zones radiating from the optical axis of the lens to some radius $R_D$ on the lens;
configured to produce constructive interference in at least five consecutive diffractive orders within a range of vision, the five consecutive diffractive orders including a lowest diffractive order, an extended intermediate diffractive order, an intermediate diffractive order, an extended near diffractive order, and a highest diffractive order, wherein: the highest diffractive order corresponds to a near focus for near vision, a lowest diffractive order corresponds to a distance focus for distance vision, the extended intermediate diffractive order corresponds to an extended intermediate focal point, the intermediate diffractive order corresponds to an intermediate focal point, and the extended near diffractive order corresponds to an extended near focal point; and
having an Optical Path Difference (OPD) described with the following formula:

$$OPD(X) = \begin{cases} \Phi_{11} + \dfrac{(X - X_0)(\Phi_{12} - \Phi_{11} + n\lambda)}{\Delta X} & X_0 \leq X < X_1 \\ \Phi_{21} + \dfrac{(X - X_1)(\Phi_{22} - \Phi_{21} + n\lambda)}{\Delta X} & X_1 \leq X < X_2 \\ \Phi_{31} + \dfrac{(X - X_2)(\Phi_{32} - \Phi_{31} + n\lambda)}{\Delta X} & X_2 \leq X < X_3 \\ \Phi_{41} + \dfrac{(X - X_3)(\Phi_{42} - \Phi_{42} + n\lambda)}{\Delta X} & X_3 \leq X < X_4 \end{cases}$$

Where $\Delta X = \dfrac{2\lambda}{ADD}$ $X_0 = 4 \Delta X \, \text{Int}\left(\dfrac{X}{4 \Delta X}\right)$ $X_1 = X_0 + \Delta X$ $X_2 = X_0 + 2 \Delta X$ $X_3 = X_0 + 3 \Delta X$ ADD is the desired additional power at the highest diffractive order and n is an integer.

2. The intraocular lens of claim 1, wherein the OPD is further modified with the following formula:

$$OPD(X) = \alpha + \beta X + \gamma X^2 + \delta X^3 \quad R_D^2 \leq X \leq R^2$$

Where $\alpha$, $\beta$, $\gamma$, and $\delta$ coefficients of the polynomials to be optimized for optimal performance of the lens and R is the radius of the lens.

3. The intraocular lens of claim 1, wherein n=1 resulting in five consecutive diffractive orders being +4, +5, +6, +7, and +8 and the lens being achromatized.

4. An intraocular lens comprising:
a lens having an anterior surface and a posterior surface and
a diffractive profile disposed on at least one of the anterior surface and the posterior surface, the diffractive profile comprising one or more annular zones about the optical axis of the lens, where each annular zone having four annular subzones, where each annular subzone comprises a diffractive step, the annular zones radiating from the optical axis of the lens to some radius $R_D$ on the lens;
configured to produce constructive interference in at least five consecutive diffractive orders within a range of vision, the five consecutive diffractive orders including a lowest diffractive order, an extended intermediate diffractive order, an intermediate diffractive order, an extended near diffractive order, and a highest diffractive order, wherein: the highest diffractive order corresponds to a near focus for near vision, a lowest diffractive order corresponds to a distance focus for distance vision, the extended intermediate diffractive order corresponds to an extended intermediate focal point, the intermediate diffractive order corresponds to an intermediate focal point, and the extended near diffractive order corresponds to an extended near focal point; and having an Optical Path Difference (OPD) described with the following formula:

$$OPD(X) = \begin{cases} \sum_{1}^{N} A_i \cos(i\Omega X + \Psi_i) & X \leq R_D^2 \\ \alpha + \beta X + \gamma X^2 + \delta X^3 & R_D^2 \leq X \leq R^2 \end{cases}$$

Where $\Omega = \dfrac{\pi ADD}{\lambda}$ the values of N, $A_i$, $\psi_i$, $\alpha$, $\beta$, $\gamma$, and $\delta$ are all known in art, ADD is the additional power, and R is the radius of the lens.

5. The intraocular lens of claim 4, wherein the number of sinusoidal Fourier harmonics is at least twelve.

\* \* \* \* \*